United States Patent
Sarhan

(10) Patent No.: US 10,470,669 B2
(45) Date of Patent: Nov. 12, 2019

(54) CONTACTLESS MEASUREMENT, MONITORING AND COMMUNICATION OF BODILY FUNCTIONS OF INFANTS AND OTHER HELPLESS INDIVIDUALS

(71) Applicant: Sameh Sarhan, Santa Clara, CA (US)

(72) Inventor: Sameh Sarhan, Santa Clara, CA (US)

(73) Assignee: Xtrava Inc, Santa Clara, CA (US)

( * ) Notice: Subject to any disclaimer, the term of this patent is extended or adjusted under 35 U.S.C. 154(b) by 0 days.

(21) Appl. No.: 15/453,911

(22) Filed: Mar. 9, 2017

(65) Prior Publication Data
US 2017/0258339 A1  Sep. 14, 2017

Related U.S. Application Data

(60) Provisional application No. 62/306,463, filed on Mar. 10, 2016.

(51) Int. Cl.
*A61B 5/0205* (2006.01)
*A61B 5/00* (2006.01)
*H04W 4/70* (2018.01)

(52) U.S. Cl.
CPC ........ *A61B 5/02055* (2013.01); *A61B 5/0002* (2013.01); *A61B 5/6804* (2013.01); *H04W 4/70* (2018.02); *A61B 5/4806* (2013.01); *A61B 2503/04* (2013.01); *A61B 2560/0242* (2013.01)

(58) Field of Classification Search
CPC . A61B 5/0008; A61B 5/01; A61B 2560/0412; A61B 2503/04; A61B 5/6808; A61F 13/42; A61F 13/15; G08B 21/00; G08B 23/00
See application file for complete search history.

(56) References Cited

U.S. PATENT DOCUMENTS 8,274,393 B2 † 9/2012 Ales
2005/0245839 A1* 11/2005 Stivoric .................. G06F 19/00
600/549

\* cited by examiner
† cited by third party

*Primary Examiner* — Christine H Matthews

(57) ABSTRACT

A system permits non-invasive measurement and wireless reporting of bodily functions of a subject wearing a diaper and an outer layer of clothing outside the diaper. The system comprises a butterfly housing which houses a plurality of sensors, a processor, a memory, and wireless circuitry. The butterfly housing has two double-arc shaped projections. Each double-arc shaped projection extends from an opposing side of the housing at a perimeter of the butterfly housing and has associated therewith a coupling clip. Each double-arc shaped projection and the associated coupling clip is configured to sandwich the outer layer of clothing to removably couple the butterfly housing to the outer layer of clothing without necessitating any modification to the outer layer of clothing. Every measurement of the bodily functions occurs without any direct contact between a skin of the subject and the butterflying housing.

10 Claims, 5 Drawing Sheets

CONTACTLESS MEASUREMENT, MONITORING AND COMMUNICATION OF BODILY FUNCTIONS OF INFANTS AND OTHER HELPLESS INDIVIDUALS

CROSS-REFERENCE TO RELATED APPLICATION

Priority is claimed under 37 CFR 1.78 and 35 USC 119(e) to U.S. Provisional Application 62/306,463 (XT1603101), filed 10 Mar. 2016), which is incorporated by reference.

TECHNICAL FIELD

This disclosure relates generally to wearable electronic measurement, monitoring, and communication equipment. More specifically, this disclosure relates to wearable electronic measurement, monitoring and automated communication equipment for infants, babies, children, and adults who may not be able to adequately care for themselves.

BACKGROUND

During the past several years, there have been many products introduced to allow monitoring of infants and others for reasons of safety. Parents and others are able to monitor subjects who are located in different rooms of a dwelling or in completely different locations. Wired intercom systems that existed more than 60 years ago have been replaced by or supplemented with handy wireless equipment. More recently, communication for monitoring purposes has been supplemented with remote monitoring of bodily functions such as breathing and heart rate. Remote vital sign monitoring of cardiac and other patients by professional organizations has been supplemented with low cost equipment for consumers.

BRIEF SUMMARY

This Brief Summary is provided as a general introduction to the Disclosure provided by the Detailed Description and Figures, summarizing some aspects of the disclosed invention. It is not a detailed overview of the Disclosure, and should not be interpreted as necessarily identifying key elements of the invention, or otherwise characterizing the scope of the invention disclosed in this Patent Document.

This disclosure covers novel ideas to expand upon existing equipment that measures and remotely monitors bodily functions. Additional ideas, when implemented, permit the monitoring equipment and systems to be more practical. For instance, the apparatus ("Instrument") and overall system disclosed herein to measure and communicate life signs and other functions of infants and others "Subjects"is not attached directly to or in contact with the Subject, or even to any diaper, but rather, to any other layer of the Subject's clothing. Novel and/or modern scientific and engineering methods, used singly and in combination, make this contactless improvement possible.

The specific instrument, mainly for infants and others needing monitoring of bodily function and environment, is contained in an intrinsically safe and attractive enclosure. The enclosure shape may not only be attractive, but can facilitate measurements and communication. Multiple quantities and types of sensors "Distributed Sensing" provide redundancy and reliability of bodily function measurements and facilitate removing the need for direct bodily contact.

Bodily functions that could be measured, monitored, and communicated, including in real time include temperature, heart rate, electrocardiogram, blood glucose concentration, breathing rate, coughing, sneezing, wheezing, gagging, edema, obstructed airway, reflux, regurgitation, vomiting, miscellaneous motion, position, water retention, bladder abundance, clothing wetness, stomach abundance, and sleep patterns. Measurements of environment may include sounds, temperature, and light, including UV. Apparatus to implement these measurements and communication to the user could include multiple 3-axis accelerometers, magnetic eddy current sensors, electrostatic sensing elements, microphones, temperature, sensors, light/UV sensors, and RF Wireless. Interpretation of raw data could be implemented with the aid of advanced automated machine learning techniques. Machine learning and other calculation tasks could be distributed among the apparatus attached to the Subject's clothing and other system building blocks, such as local video and communication devices and even the user's smart phone.

Other aspects, features and advantages of the invention will be apparent to those skilled in the art from the following Disclosure.

BRIEF DESCRIPTION OF DRAWINGS

For a more complete understanding of this disclosure and its features, reference is now made to the following description, taken in conjunction with the accompanying drawings, in which.

DETAILED DESCRIPTION

The various figures, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system. For instance, although the figures show the Instrument enclosure with a shape that could be construed to resemble a butterfly or other winged creature, the enclosure can have a side variety of shapes. The attachment mechanism shown and later described is but one example of a safe means to attach the Instrument to clothing.

In general, this disclosure describes apparatus that attaches to the clothing of the subject being monitored ("Subject"), obtains real time information pertaining to a significant variety of bodily functions and environmental conditions, and communicates said information immediately or later to interested parties and/or recording equipment ("User") who may be co-located or at any remote location.

Depending upon the implementation, this technique can provide significant benefits in a range of fields, such as care for infants, small children, elderly, the mentally challenged, ill and injured, and others who cannot fully care for themselves.

Figure 1:
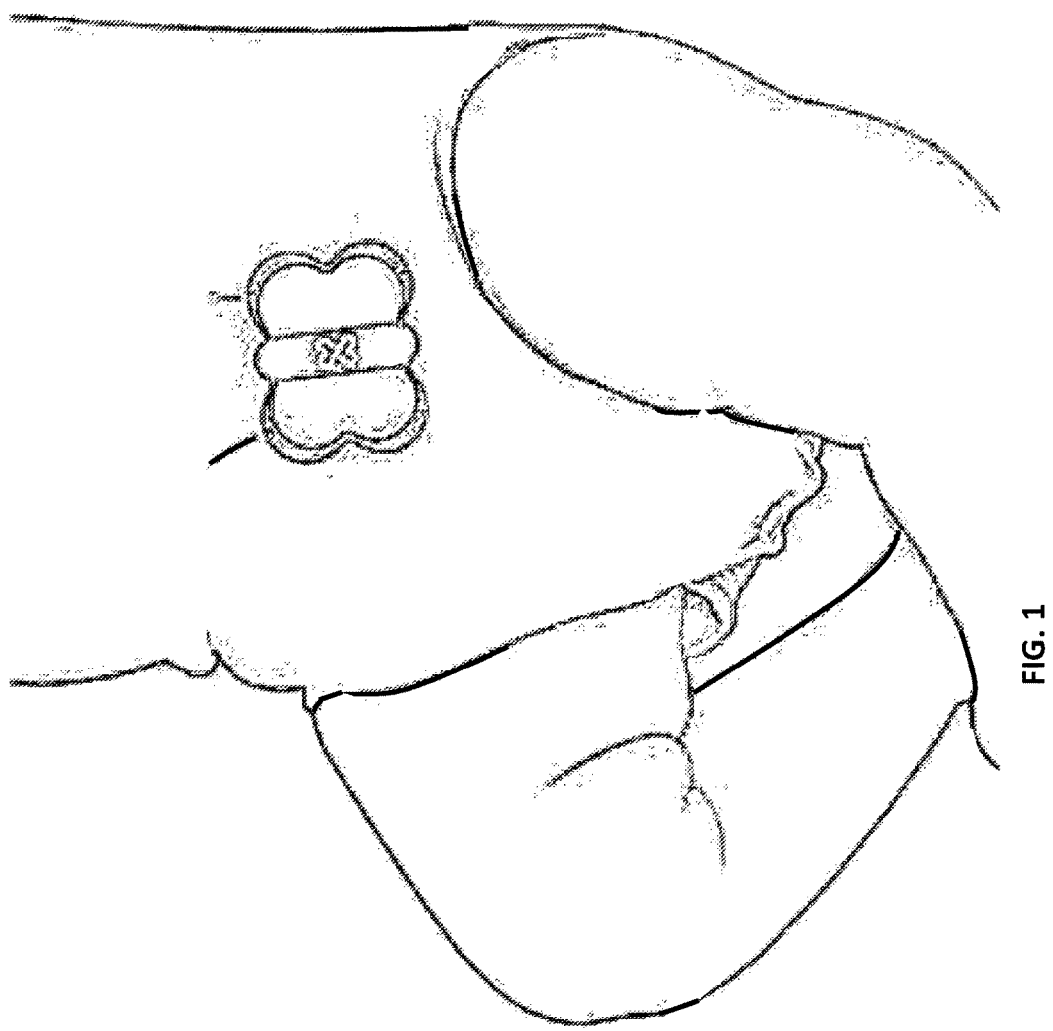
FIG. 1 shows an infant wearing an example instrument apparatus attached to clothing worn over a diaper.

FIG. 1 shows the example instrument apparatus attached to "onesie"apparel worn by an infant over its diaper. This Instrument could also be attached to clothing worn by a baby, a child, an adult, or even an animal. Although it looks like a decoration or toy (in this example resembling a butterfly or other small winged creature) and is as safe as a properly designed toy, it is loaded with technology that communicates with the outside world and assesses a host of bodily functions and environmental conditions. Safety features include but are not limited to enclosure materials used in toys, the lack of sharp corners, a size that is too large for a baby to swallow, and an ultra-safe level of emissions.

Figure 2:
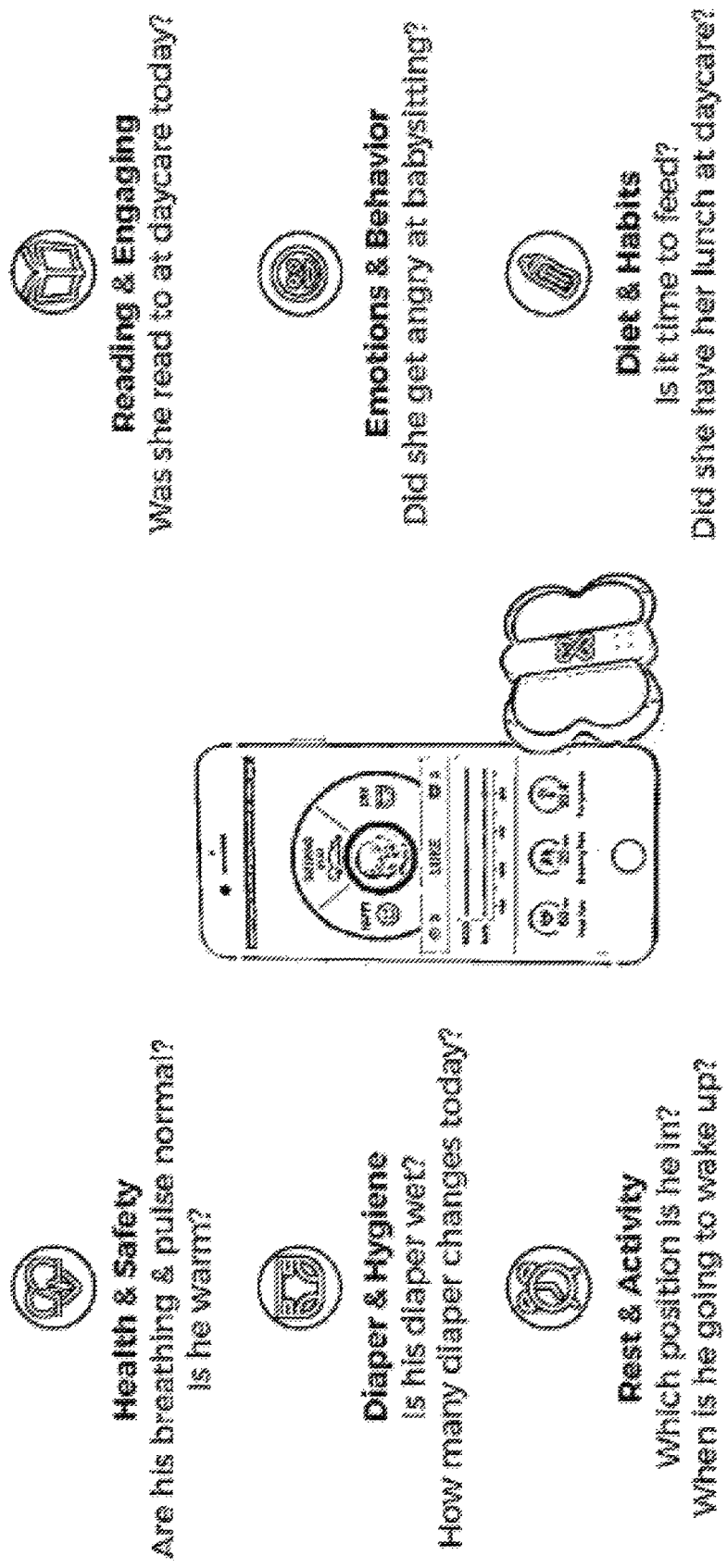
FIG. 2 shows examples of information about said infant that could be measured by the Instrument shown in FIG. 1 and communicated locally and thence world-wide.

FIG. 2 illustrates an example User interface employing a smart phone, and the Subject sensor apparatus itself. It also shows a partial list of service functions performed with the aid of the apparatus.

Figure 3:
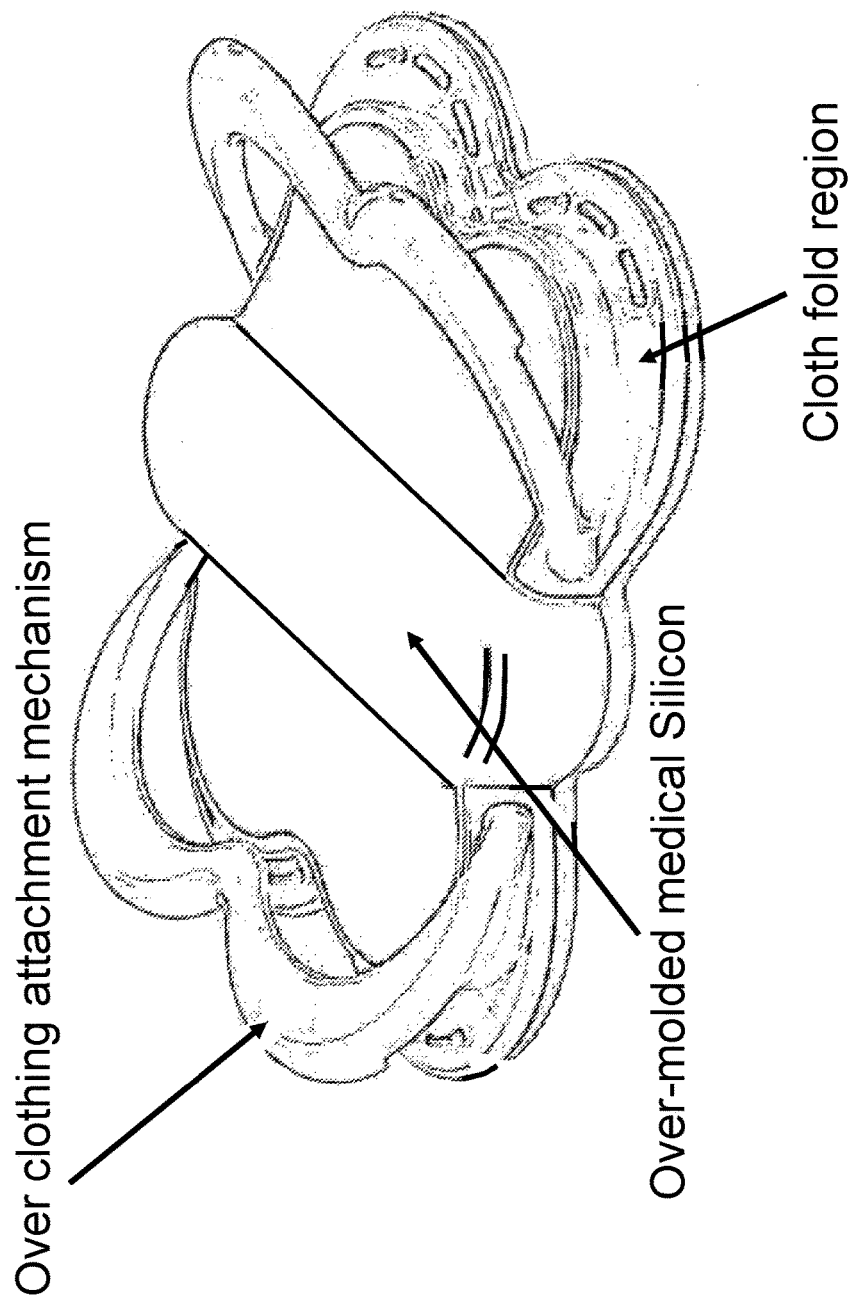
FIG. 3 shows details of an example mechanism to safely attach said Instrument to any clothing layer.

FIG. 3 shows the Instrument apparatus sensors, measuring Instrument and communication apparatus as seen from the side that faces away from the Subject. The overall size is large enough that it cannot be swallowed by a baby or small child. The material composition is a "medical" Silicon that is used for teething toys. The clothing cloth fits into the fold region at the edges of the "wings", and the attachment mechanisms, shown in the open state, clamps to the clothing.

Figure 4:
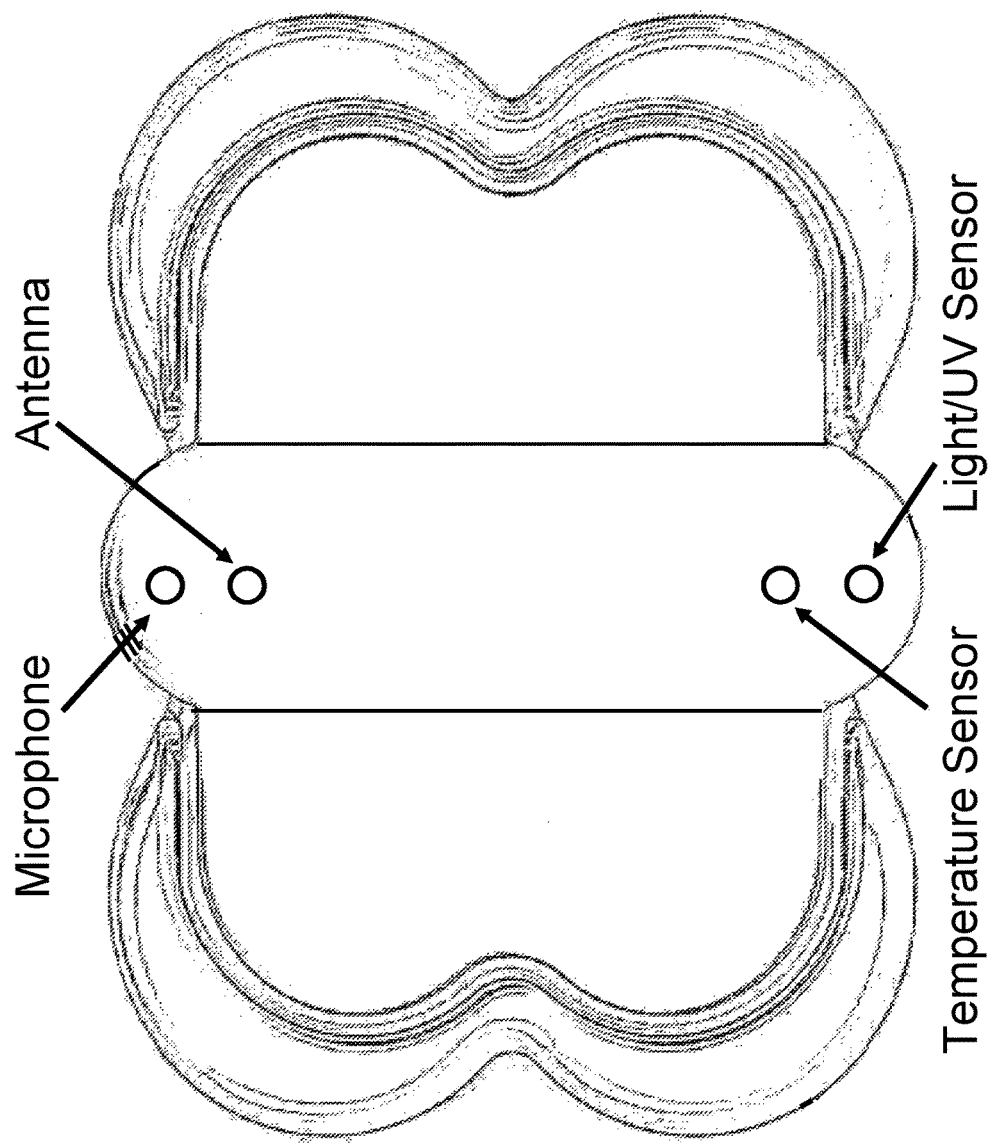
FIG. 4 shows the side of said Instrument that faces away from said infant, with the mounting rails closed and without being attached to clothing. Also shown are possible locations of various sensors and RF communications antenna.

FIG. 4 also shows the Instrument, containing sensor, measuring circuitry and data handling circuitry as seen from the side that faces away from the Subject. The attachment mechanism is shown in the closed condition. Also shown is the region where the RF communications antenna and various example facilities may be located inside the enclosure. The Light/UV sensor is located at one end of the Instrument, as an indicator of normal ambient light on the Subject, as well as damaging ultra-violet radiation. An additional sensor for infrared radiation could also be added. At the other end of the Instrument is the microphone that could monitors ambient sounds of the subject and others. Next to the light/UV sensor is an ambient temperature measurement sensor. For the light, temperature, and sound sensors, the Silicon enclosure has modified properties to pass light and sound and temperature information but still maintain integrity such as waterproofing and safety.

Figure 5:
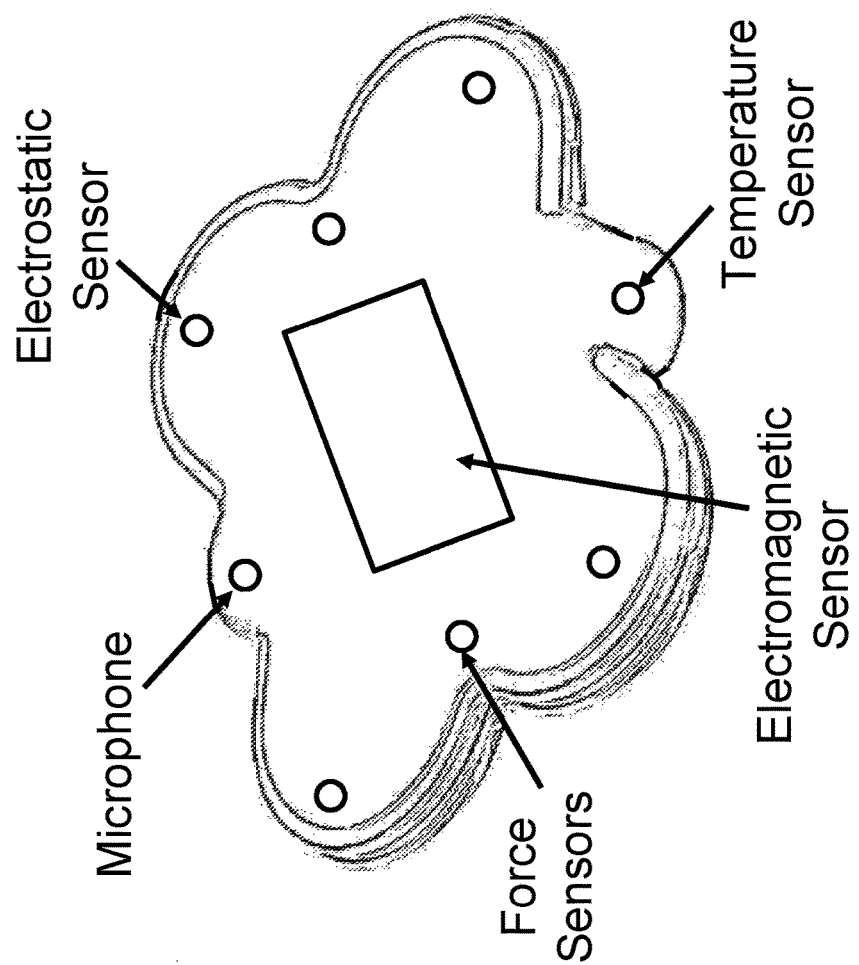
FIG. 5 shows the side of said Instrument that faces toward said infant, showing possible locations of various sensors that gather information about him/her.

FIG. 5 shows the side of the Instrument and communication apparatus that faces the Subject. The microphone on this side picks up internal sounds from the Subject's body, and the temperature sensor picks up internal "core" body temperature. The electromagnetic and electrostatic sensors within the enclosure could pick up motion and properties of internal organs and fluids. The items marked "force sensors" are 3-axis accelerometers that also help determine motion of internal organs, but mainly sense motion and position of the body as a whole.

The different types of sensors, and multiple sets of sensors of the same type provide measurements of many bodily functions as well as additional accuracy, redundancy and reliability of said measurements.

The sensors and communication devices located within this Instrument apparatus emit fields that are intrinsically safe as defined by recognized safety standards. Emissions from the Instrument that permeate the Subject's body are several orders of magnitude smaller than the minimum recommended by the Federal Communications Commission and other widely recognized standards and regulatory institutions and agencies.

Other embodiments could be implemented in any other suitable manner. For example, other enclosure materials than that mentioned in this disclosure may have all the desired properties to be safe for babies. The apparatus may have different sizes, shapes, and fastening mechanisms, and may be placed in different positions on the body. The clothing could be a "onesie"piece as shown or any other type or style. The Subject could be an infant, any other variety of human, or non-human.

The details provided in the foregoing description and figures describe in part particular implementations of the systems for performing the functions explained in this disclosure. Other embodiments could be implemented in any other suitable manner. For example, the figures show a particular module physical size and other physical configurations. This disclosure and as-built example equipment report on and utilize a standard interface package—the size, as opposed to other sizes and shapes. These configurations are for illustration only. Other embodiments could use different key system blocks, depending upon the implementation. Moreover, measuring pulse and respiration rate within the body only two examples of what the methods of this disclosure can perform. Other embodiments could be implemented in any other suitable manner. For example, this disclosure describes particular sizes, shapes, and other values. These values are for illustration only.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system that permits non-invasive measurement and wireless reporting of bodily functions of a subject wearing a diaper and an outer layer of clothing outside the diaper, the system comprising:

a plurality of sensors, a processor, a memory, and wireless circuitry, the memory containing machine readable instructions configured to be executed by the processor to measure the bodily functions using the plurality of sensors, the wireless circuitry being configured to wirelessly transmit the measured bodily functions to an external device;

a butterfly housing for housing the sensors, the processor, the memory, and the wireless circuitry; the butterfly housing having two double-arc shaped projections, each double-arc shaped projection extending from an opposing side of the housing at a perimeter of the butterfly housing and having associated therewith a coupling clip; each double-arc shaped projection and the associated coupling clip being configured to sandwich the outer layer of clothing to removably couple the butterfly housing to the outer layer of clothing without necessitating any modification to the outer layer of clothing;

wherein:

the plurality of sensors includes at least two microphones, one of the at least two microphones configured to face the subject and another of the at least two microphones configured to face away from the subject; and every measurement of the bodily functions is configured to occur without any direct contact between a skin of the subject and the butterfly housing.

2. A system that permits non-invasive measurement and wireless reporting of bodily functions of a subject wearing a diaper and an outer layer of clothing outside the diaper, the system comprising:

a plurality of sensors, a processor, and a memory, the memory containing machine readable instructions configured to be executed by the processor to measure the bodily functions using the plurality of sensors;

a butterfly housing for housing the sensors, the processor, the memory, and the wireless circuitry, the butterfly housing having two double-arc shaped projections, each double-arc shaped projection extending from an opposing side of the housing at a perimeter of the butterfly housing and having associated therewith a coupling clip, each double-arc shaped projection and the associated coupling clip being configured to sandwich the outer layer of clothing to removably couple the butterfly housing to the outer layer of clothing without necessitating any modification to the outer layer of clothing;

wherein, every measurement of the bodily functions is configured to occur without any direct contact between a skin of the subject and the butterfly housing.

3. A system as defined in claim 2, wherein the butterfly housing includes silicon.

4. A system as defined in claim 3 wherein the bodily functions include vital signs.

5. A system as defined in claim 4 wherein the bodily functions include position and motion.

6. A system as defined in claim 5 wherein the bodily functions include at least one of respiration rate and heart rate.

7. A system as defined in claim 6 wherein the plurality of sensors measure environmental temperature, light level, light wavelength, and sound characteristics.

8. A system as defined in claim 7 wherein the plurality of sensors include multiple types of sensors configured to detect the same bodily function.

9. A system as defined in claim 8 wherein the bodily functions include urination.

10. A system as defined in claim 2 wherein the butterfly housing is devoid of sharp corners.

* * * * *